(12) United States Patent
Wang

(10) Patent No.: US 8,821,809 B2
(45) Date of Patent: Sep. 2, 2014

(54) TEST STRIP READER FOR DETECTING BIOREACTION CHANGES

(75) Inventor: Jiann-Hua Wang, New Taipei (TW)

(73) Assignee: Yonglin Healthcare Foundation, New Taipei (TW)

( * ) Notice: Subject to any disclaimer, the term of this patent is extended or adjusted under 35 U.S.C. 154(b) by 41 days.

(21) Appl. No.: 13/480,425

(22) Filed: May 24, 2012

(65) Prior Publication Data

US 2012/0300211 A1 Nov. 29, 2012

(51) Int. Cl.
*G01N 33/00* (2006.01)
*G01N 21/84* (2006.01)

(52) U.S. Cl.
CPC .................................. *G01N 21/8483* (2013.01)
USPC ..................... 422/404; 422/82.05; 422/82.06; 422/400

(58) Field of Classification Search
USPC ............................. 422/400, 404, 82.05, 82.06
See application file for complete search history.

(56) References Cited

U.S. PATENT DOCUMENTS 6,180,409 B1 * 1/2001 Howard et al. ................. 436/46

* cited by examiner

*Primary Examiner* — Sam P Siefke
(74) *Attorney, Agent, or Firm* — Novak Druce Connolly Bove + Quigg LLP

(57) ABSTRACT

A test strip reader for reading a test result of a test strip plate or cassette is provided. The test strip plate or cassette includes a test strip and is configured for generating a control line or a test line in the test strip according to the test result. The test strip plate or cassette reader includes a light source, a driver configured for driving the light source to emit light to a section of the test strip corresponding to the control line or the test line, a photo detector configured for receiving light reflected from the section and generating a detecting signal corresponding to the test result, a signal processor configured for processing the detecting signal to obtain the test result and generating a corresponding result signal, and a display configured to display the test result based upon the result signal.

6 Claims, 7 Drawing Sheets

TEST STRIP READER FOR DETECTING BIOREACTION CHANGES

BACKGROUND

1. Technical Field

The present disclosure relates to medical devices and, particularly, to a test strip reader and a diagnostic test device having a high readability.

2. Description of Related Art

Nowadays, various test strips are developed and used to determine bioreaction changes. For example, a pregnancy test strip has been developed to determine whether a woman is pregnant by sampling the urine of the woman. If a specific line is generated after the sampling, the test result is positive and otherwise is negative. However, if the change is at a beginning state, the line is very faint and is difficult to be identified from a background of the test strip.

Therefore, it is desirable to provide a test strip reader and a diagnostic test device, which can overcome the limitations described.

DETAILED DESCRIPTION

Embodiments of the disclosure will be described in detail, with reference to the accompanying drawings.

Figure 1:
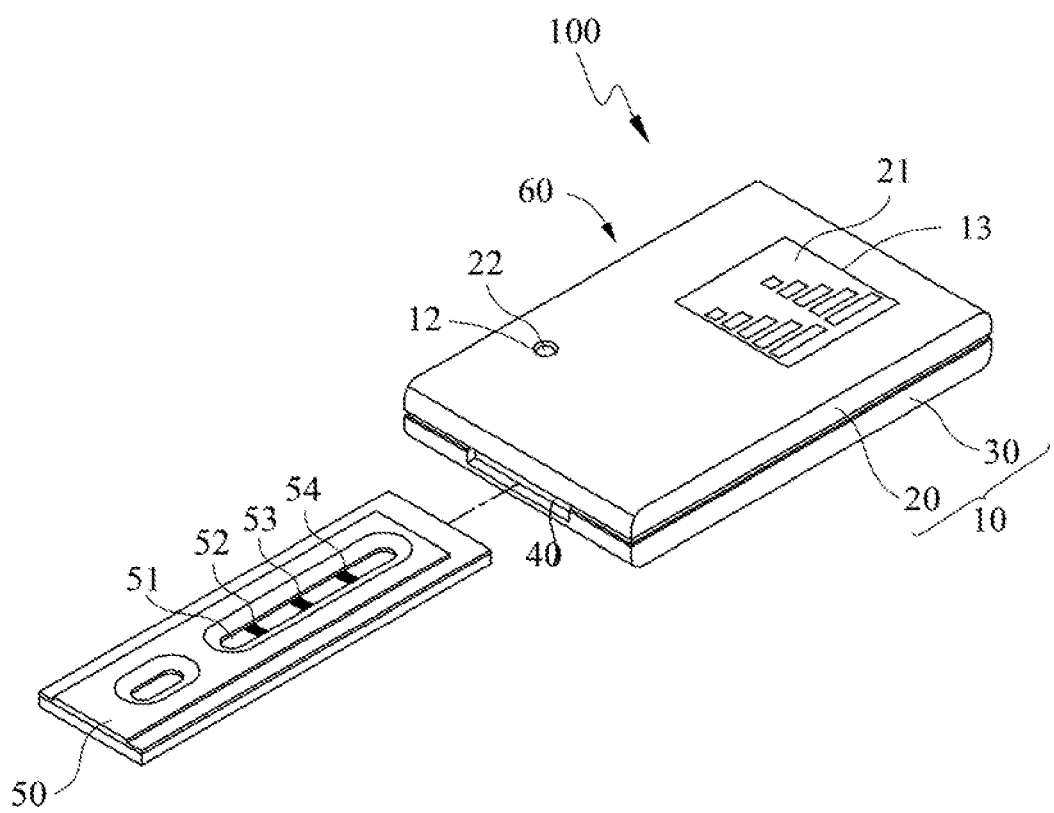
FIG. 1 is an isometric schematic view of a diagnostic test device, according to an embodiment.

Referring to FIG. 1, a diagnostic test device 100 includes a test strip plate or cassette 50 and a test strip reader 60.

The test strip plate or cassette 50 is configured for detecting bioreaction changes in urine and/or blood. In this embodiment, the test strip plate or cassette 50 has an test strip 51 and indicates a test result by generating a control line 52 and two test lines 53, 54 at specific positions of the test strip 51. Specifically, the test strip 51 has a uniform white color except reaction lines before use. However, after use, a section of the test strip 51 corresponding to the control line 52 may turn black (that is, the control line 52 is generated) to show a validity of the test strip 51. If the control line 52 does not appear, it implies that that test strip 51 is invalidated and the test result, regardless of positive or negative, is not reliable. Similarly, sections of the test strip 51 corresponding to the test lines 53, 54 may turn black (that is, the test lines 53, 54 are generated) to show a positive result. If the test lines 53, 54 do not appear, the test result is negative.

The configuration of the test strip plate or cassette 50 is not limited to this embodiment. For example, in other embodiments, the test strip plate or cassette 50 may have only one test line or only have the control line.

Figure 2:
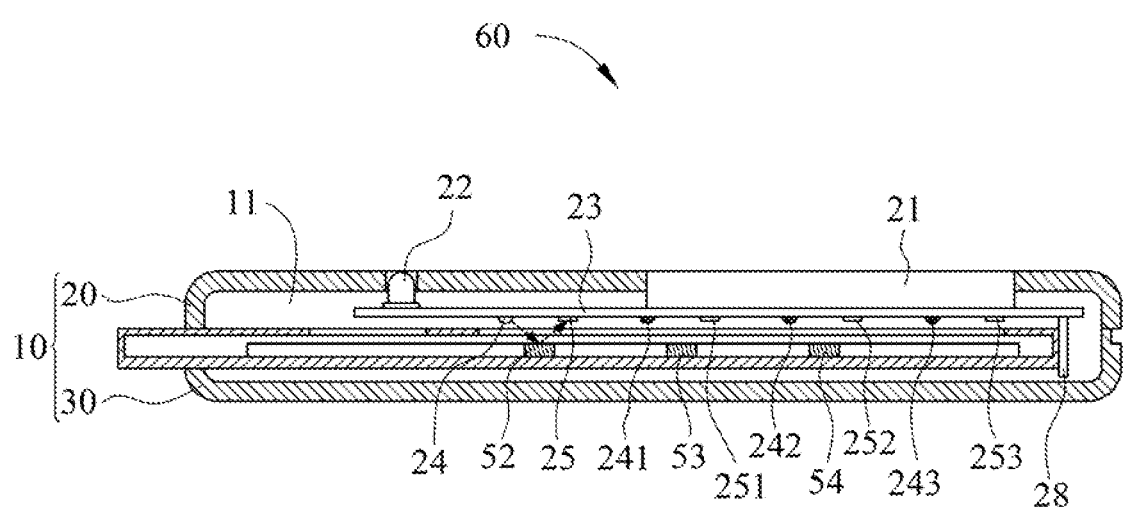
FIG. 2 is a cross-sectional schematic view of the diagnostic test device of FIG. 1, which is in a first state.

Also referring to FIG. 2, the test strip reader 60 includes a shell 10, a printed circuit board (PCB) 23, four light sources 24, 241, 242, 243, four photo detectors 25, 251, 252, 253, a display 21, a positional switch 28, and an indicator 22.

The shell 10 includes an upper cover 20 and a bottom cover 30, which are engaged with each other to form a cavity 11 therebetween and an insertion slot 40 communicating the cavity 11 with outside. The cavity 11 is for receiving the PCB 23 therein. The insertion slot 40 corresponds to the test strip plate or cassette 50 in shape and is for allowing the test strip plate or cassette 50 to be inserted into the cavity 11 for result reading. The upper cover 20 also defines a first opening 12 and a second opening 13 with appropriate configurations (e.g., shapes and positions).

Figure 3:
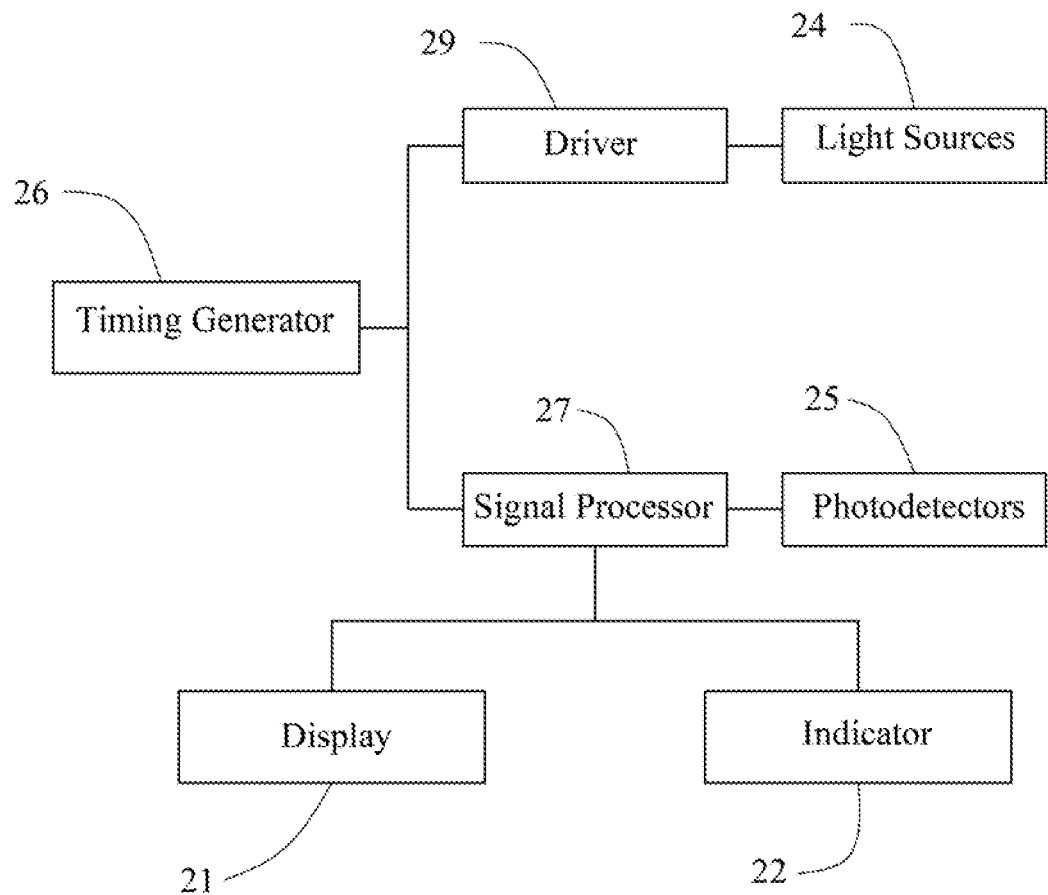
FIG. 3 is a functional diagram of the diagnostic test device of FIG. 1.

Also referring to FIG. 3, the PCB 23 forms circuits therein that can function as a timing generator 26, a driver 29, and a signal processor 27.

The timing generator 26 is configured for generating signals with time interval.

Figure 4:
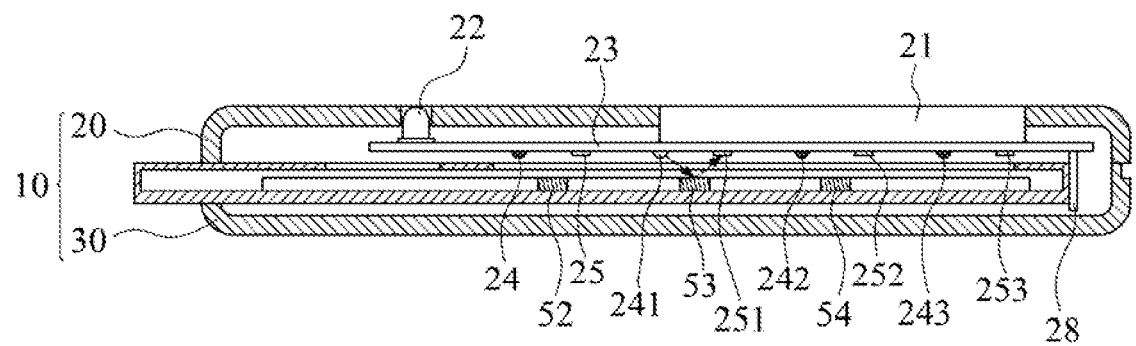
FIG. 4 is a cross-sectional schematic view of the diagnostic test device of FIG. 1, which is in a second state.
Figure 5:
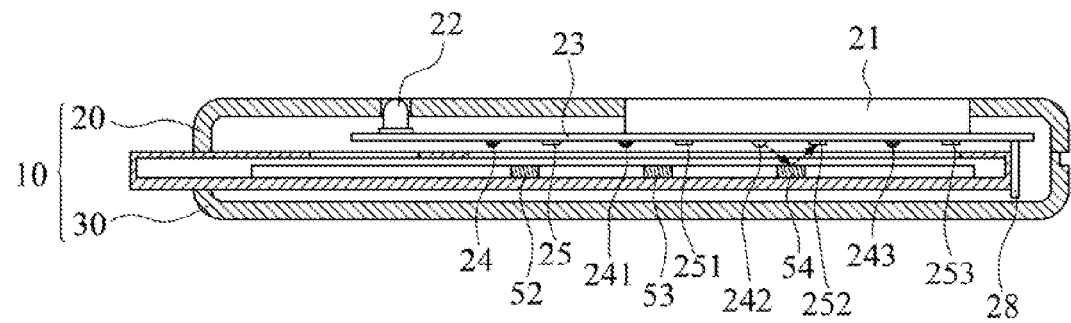
FIG. 5 is a cross-sectional schematic view of the diagnostic test device of FIG. 1, which is in a third state.
Figure 6:
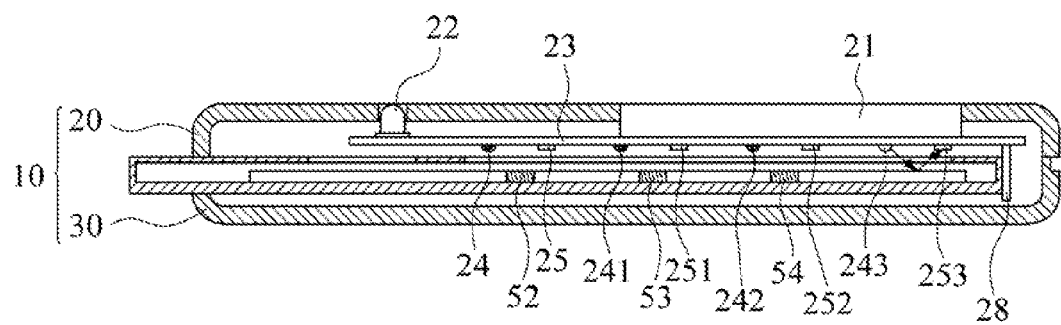
FIG. 6 is a cross-sectional schematic view of the diagnostic test device of FIG. 1, which is in a fourth state.

The light sources 24, 241, 242, 243 and the photo detectors 25, 251, 252, 253 are positioned on the PCB 23, wherein the light sources 24, 241, 242, 243 are electrically connected to the driver 29 and the photo detectors 25, 251, 252, 253 are electrically connected to the signal processor 27. The driver 29 is configured for driving the light sources 24, 241, 242, 243 to emit light in sequence according to the time-controlled signals (See FIGS. 4-6).

The light sources 24, 241, 242, 243 and the photo detectors 25, 251, 252, 253 are arranged in pairs for detecting the control line 52, the test lines 53, 54, and the background of the test strip 51, respectively. In detail, the light source 24 and the photo detector 25 are arranged such that light emitted from the light source 24 is reflected off the section of the test strip 51 corresponding to the control line 52 to the photo detector 25. The light source 241 and the photo detector 251 are arranged such that light emitted from the light source 241 is reflected off the section of the test strip 51 corresponding to the test line 53 to the photo detector 251. The light source 242 and the photo detector 252 are arranged such that light emitted from the light source 242 is reflected off the section of the test strip 51 corresponding to the test line 54 to the photo detector 252. The light source 243 and the photo detector 253 are arranged such that light emitted from the light source 243 is reflected off a background of the test strip 51 to the photo detector 253.

Reflectance of light changes with the color and color intensity of what the light is reflected off. As such, the photo detectors 25, 251, 252, 253 can detect differences in light reflected from any control line 52 and test lines 53, 54 produced, even when the control line 52 and the test lines 53, 54 are quite faint, and generating a corresponding detecting signal depending on whether or not the control line 52 and the test lines 53, 54 are produced.

The signal processor 27 is configured for reading the detecting signals from the photo detectors 25, 251, 252, 253 and processing the detecting signals to obtain a test result which is in a form of a result signal.

The display 21 is positioned on the PCB 23 and electrically connected to the signal processor 27 to read the result signal and display the test result based upon the result signal. For example, if the photo detectors 25 and 253 detect different amounts of light (i.e., changes in reflectance indicating the appearance of the control line 52 and the background of the test strip 51) the test result of the signal processor 27 is that the test strip 51 is valid, and if no change in reflectance was detected then the test strip 51 would be considered invalid. If the photo detectors 251, 252, 253 detect different amounts of light (changes in reflectance indicating the appearance of the test lines 53, 54 and the background of the test strip 51), the test result of the signal processor 27 will indicate a positive, and otherwise a negative. Thus, the display 21 can display accordingly. The display 21 is exposed outside the shell 10 via the second opening 13 for reading.

The light sources 24, 241, 242, 243 employ green light emitting diodes (LEDs) to increase a sensitivity of the detection. Specifically, a reflectance of green light changes more significantly with changes in color and color intensity of where the green light is reflected, as compared with lights at other wavelengths.

The number of the light sources and the photo detectors are not limited to this embodiment, but should be set according to the configuration of the test strip 51. For example, if the test strip plate or cassette 50 only has one control/test line, the test strip reader 60 may only employ two light sources and two photo detectors, one is for detecting the reflectance of the control/test line, and the other is for detecting the reflectance of the background of the indication zone of the test strip.

The detection of the background of the test strip 51 is for providing a basis for measuring whether there is a change in reflectance of light at the sections corresponding to the control/test lines. In other embodiments, the basis can be predetermined by experiments and calculation and input to the signal processor 27. As such, the light source and the photo detector for detecting the background of the indication zone 51 can be omitted. Even though the test strip plate or cassette 50 only has one control/test line, then only one light source and photo detector are required. Accordingly, the timing generator 26 is also necessary.

The positional switch 28 is positioned on the PCB 23 at appropriate position such that when the test strip plate or cassette 50 is at a position ready for reading, the positional switch 28 is turned on by the test strip plate or cassette 50 by a contact between the positional switch 28 and the test strip plate or cassette 50. The positional switch 28 is electrically connected to and configured for activating the timing generator 26, the driver 29, and the signal processor 27.

The indicator 22 is positioned on the PCB 23 and electrically connected to the positional switch 28 and the signal processor 27. The indicator 22 is exposed outside the shell 10 via the first opening 12 and configured for indicating states of the test strip reader 60 and the test. For example, the indicator 22 can be an LED assembly. When the positional switch 28 is turned on, the indicator 22 can emits red light to indicate that the test strip reader 60 is turned on. When the test strip plate or cassette 50 is invalid, the indicator 22 flicks with red light. When the test strip plate or cassette 50 is valid, the indicator 22 turns green. In other embodiments, the indicator 22 can give other indications for the corresponding states of the test strip reader 60 and the test, not limited to this embodiment.

Figure 7:
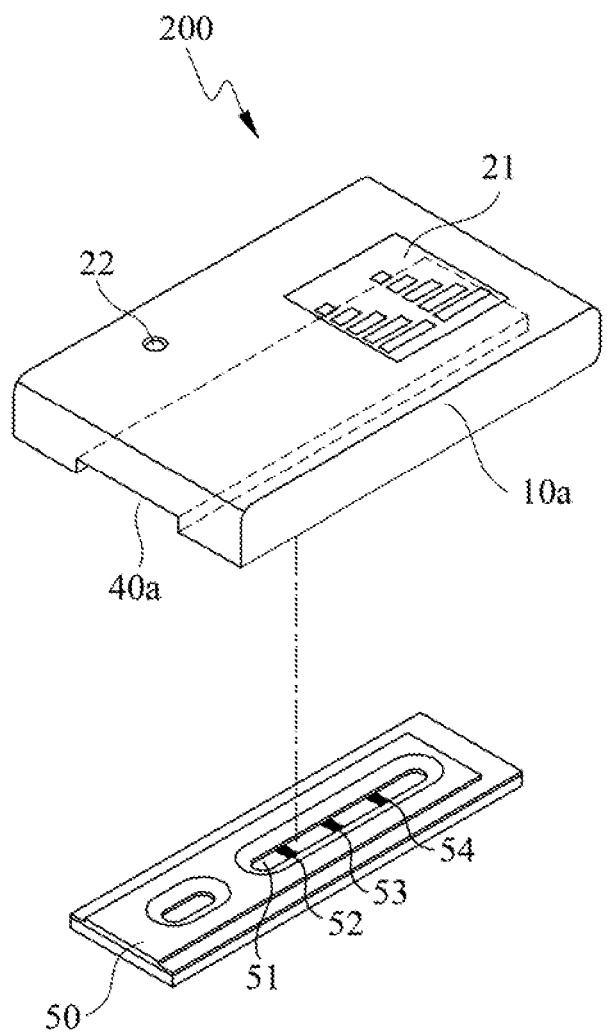
FIG. 7 is an isometric schematic view of a diagnostic test device, according to another embodiment.

Referring to FIG. 7, a diagnostic test device 200, according to another embodiment, is essentially similar to the diagnostic test device 100 but replace the shell 10 with another shell 10a. The shell 10a is essentially similar to the upper cover 20. The PCB 23 is mounted on the shell 10a with the display 21 and the indicator 22 protruding from the shell 10a. The shell 10a further defines a positioning slot 40a for positioning the test strip plate or cassette 50 at a position for reading.

Particular embodiments are shown here and described by way of illustration only. The principles and the features of the present disclosure may be employed in various and numerous embodiments thereof without departing from the scope of the disclosure as claimed. The above-described embodiments illustrate the scope of the disclosure but do not restrict the scope of the disclosure.

What is claimed is:

1. A diagnostic test device, comprising:
   a test strip plate or cassette configured for detecting pathological change, the test strip plate or cassette comprising a test strip and being configured for generating a control line and two test lines at respective specific positions of the test strip according to a test result; and
   a test strip reader comprising:
   four light sources;
   a timing generator configured for generating time-controlled signals;
   a driver configured for driving the light sources to emit lights to sections of the test strip corresponding to the control line and the test lines and to a background of the test strip, respectively, in sequence according to the time-controlled signals;
   four photo detectors configured for receiving the lights reflected from the sections of the test strip and from the background of the zone, respectively, in sequence according to the time-controlled signals and generating a detecting signal;
   a signal processor configured for processing the detecting signal to generate a result signal corresponding to the test result; and
   a display configured for display the test result according to the result signal;
   wherein the timing generator, the driver, and the signal processor are integrated into a printed circuit board (PCB), and the light sources, the photo detectors, and the display are mounted on and electrically connected to the PCB at appropriate positions.

2. The diagnostic test device of claim 1, wherein the test strip plate or cassette reader further comprises a shell, the shell defines a cavity receiving the PCB, the light sources, and the photo detectors, the shell defines an insertion slot to allow the test strip plate or cassette to be inserted into the cavity for reading the test result, and the shell also defines an opening to allow the display to be exposed from the shell therethrough.

3. The diagnostic test device of claim 1, wherein the test strip plate or cassette reader further comprises a shell, the PCB is mounted on the shell, and the shell further defines a positioning slot for positioning the test strip plate or cassette at a position ready for reading the test result.

4. The diagnostic test device of claim 1, wherein the test strip plate or cassette reader further comprises a positional switch positioned on the PCB at appropriate position such that when the test strip plate or cassette is at a position ready for reading the test result the positional switch is turned on by the test strip plate or cassette by a contact between the positional switch and the test strip plate or cassette, and the positional switch is electrically connected to and configured for activating the timing generator, the driver, and the signal processor.

5. The diagnostic test device of claim 4, wherein the test strip plate or cassette reader further comprises an indicator, the indicator is positioned on the PCB and electrically connected to the positional switch and the signal processor, and the indicator is configured for indicating states and the test.

6. The diagnostic test device of claim 5, wherein the indicator give a first indication when the test strip plate or cassette reader is turned on, a second indication when the test strip plate or cassette is valid, and a third indication when the test strip plate or cassette is invalid.

* * * * *